US012680195B2

(12) United States Patent
Niikura et al.

(10) Patent No.: US 12,680,195 B2
(45) Date of Patent: ***Jul. 14, 2026

(54) METHOD FOR PROMOTING DIVERSIFICATION OF ANTIBODY VARIABLE REGION

(71) Applicant: Chiome Bioscience Inc., Tokyo (JP)

(72) Inventors: Keisuke Niikura, Tokyo (JP); Yosuke Kamimura, Tokyo (JP)

(73) Assignee: Chiome Bioscience Inc., Tokyo (JP)

( * ) Notice: Subject to any disclaimer, the term of this patent is extended or adjusted under 35 U.S.C. 154(b) by 864 days.

This patent is subject to a terminal disclaimer.

(21) Appl. No.: 18/149,439

(22) Filed: Jan. 3, 2023

(65) Prior Publication Data

US 2023/0220049 A1 Jul. 13, 2023

Related U.S. Application Data

(63) Continuation of application No. 16/484,061, filed as application No. PCT/JP2018/004697 on Feb. 9, 2018, now Pat. No. 11,572,402.

(30) Foreign Application Priority Data

Feb. 10, 2017 (JP) ................................. 2017-023001

(51) Int. Cl.
*C40B 50/06* (2006.01)
*C07K 16/00* (2006.01)
(52) U.S. Cl.
CPC .............. *C40B 50/06* (2013.01); *C07K 16/00* (2013.01)
(58) Field of Classification Search
None
See application file for complete search history.

(56) References Cited

U.S. PATENT DOCUMENTS

| | | |
|---|---|---|
| 2011/0070650 A1 | 3/2011 | Ohta et al. |
| 2015/0167011 A1 | 6/2015 | Li |
| 2017/0058029 A1 | 3/2017 | Hashimoto et al. |

FOREIGN PATENT DOCUMENTS

| | | |
|---|---|---|
| EP | 1559318 A1 | 8/2005 |
| JP | 2006-109711 A | 4/2006 |
| JP | 4214234 B | 1/2009 |
| JP | 2009-060850 A | 3/2009 |
| JP | 4478577 B | 6/2010 |
| WO | WO 02/100998 A2 | 12/2002 |
| WO | WO 2008/047480 A1 | 4/2008 |
| WO | WO 2009/029315 A2 | 3/2009 |

OTHER PUBLICATIONS

Arakawa et al. Activation-induced cytidine deaminase-mediated hypermutation in the DT40 cell line. The Royal Society, Biological Sciences pp. 639-644, Nov. 13, 2008.

(Continued)

*Primary Examiner* — Christian C Boesen
(74) *Attorney, Agent, or Firm* — Knobbe Martens Olson & Bear LLP

(57) ABSTRACT

A method for promoting diversification of variable regions of an antibody, particularly a method for promoting diversification of the amino acid sequences of variable regions of an antibody generated by an avian B cell population, the method including suppressing the PI3Kα activity of each avian B cell comprised in the avian B cell population expressing the antibody.

3 Claims, 5 Drawing Sheets

Specification includes a Sequence Listing.

(56) References Cited

OTHER PUBLICATIONS

Backer, "The Regulation of Class IA PI 3-Kinases by Inter-Subunit Interactions", Curr Top Microbiol Immunol. 2010 ; 346: 87-114.

Baracho et al. Emergence of the PI3-kinase pathway as a central modulator of normal and aberrant B cell differentiation, Current Opinion in Immunology, pp. 178-183, Feb. 1, 2011.

Barreto et al., "C-Terminal Deletion of AID Uncouples Class Switch Recombination from Somatic Hypermutation and Gene Conversion", Molecular Cell, vol. 12, 501-508, Aug. 2003.

Chen et al., "Imbalanced PTEN and Phosphoinositide 3-kinase signaling impairs class switch recombination", J Immunol. Dec. 1, 2015; 195(11): 5461-5471.

Extended European Search Report in European Patent Application No. 18750887.4 issued on Nov. 12, 2020.

Heltemes-Harris et al., "Activation induced deaminase-mediated class switch recombination is blocked by anti-IgM signaling in a phosphatidylinositol 3-kinase-dependent fashion", Mol Immunol. Mar. 2008 ; 45(6): 1799-1806.

Kanehiro et al., "In vitro antibody screening system using a chicken B cell line, DT40-SW: Improvement of mutation frequency", Abstract of Annual Meeting, The society for Biotechnology Japan p109 2008.

Kincade and Cooper, "Immunoglobulin A: Site and sequence of expression in developing chicks" Science, vol. 179, pp. 398-400, 1973 (Year: 1973).

Leighton et al. A diverse repertoire of human immunoglobulin variable genes in a chicken B cell line is generated by both gene conversion and somatic hyper mutation. Article, Frontier in Immunology pp. 1-8, vol. 6, Mar. 20, 2016.

Luna-Acosta et al. "Direct antiapoptotic effects of growth hormone are mediated by PI3k/Akt pathway in the chicken bursa of Fabricius" General and Comparative Endocrinology 224 (2015) 148-159 (Year: 2015).

Magari et al. Enhancement of hypermutation frequency in the chicken B cell line DT40 for efficient diversification of the antibody repertoire. Article, Biochemical and Biophysical Research Communications, pp. 353-357, Apr. 15, 2010.

Noira et al. Altering the pathway of immunoglobulin hypermutation by inhibiting uracil-DNA glycosylase. Article, Nature Publishing Group, vol. 419, pp. 43-47, Sep. 2002.

Okkenhaug et al., "PI3K Signaling in Normal B Cells and Chronic Lymphocytic Leukemia", Current Topics in Microbiology and Immunology (2016) 393: 123-142.

Omori et al. Phosphatidylinositol 3-kinase (PI3K) Signaling and Regulation of the Antibody Response. Article, Cell Cycle pp. 397-402, Feb. 26, 2007.

Omori et al. Regulation of Class-Switch Recombination and Phasma Cell Differentiation by Phosphatidylinositol 3-Kinase Signaling. Article, Immunity, pp. 545-557, Aug. 15, 2006.

Omori et al., "Regulation of Class-Switch Recombination and Plasma Cell Differentiation by Phosphatidylinositol 3-Kinase Signaling", Immunity 25, 545-557, Oct. 2006.

Schötz. Diversification of the immunoglobulin genes: analysis of the molecular mechanisms in the chicken B cell line DT40, Dissertation, Sep. 2, 2009.

Seo et al., "Rapid generation of specific antibodies by enhanced homologous recombination Nature biotech", Nature Biotechnology, vol. 23, No. 6, Jun. 2005.

Thapa et al. Modulation of PI3K signaling by mTOR complexes in antibody responses of B lymphoid cells, Article, Korean Association for Laboratory Animal Science, pp. 191, 2018.

Wentink et al., "Genetic defects in PI3Kδ affect B-cell differentiation and maturation leading to hypogammaglobulineamia and recurrent infections", Clinical Immunology 176 (2017) 77-86.

Werner et al Role of PI3K in the generation and Survival of B cells. Article, Immunological Reviews, pp. 55-71, 2010.

Zhang et al., "B Cell-specific Deficiencies in mTOR Limit Humoral Immune Responses", J Immunol. Aug. 15, 2013; 191(4): 1692-1703.

[Figure 1]
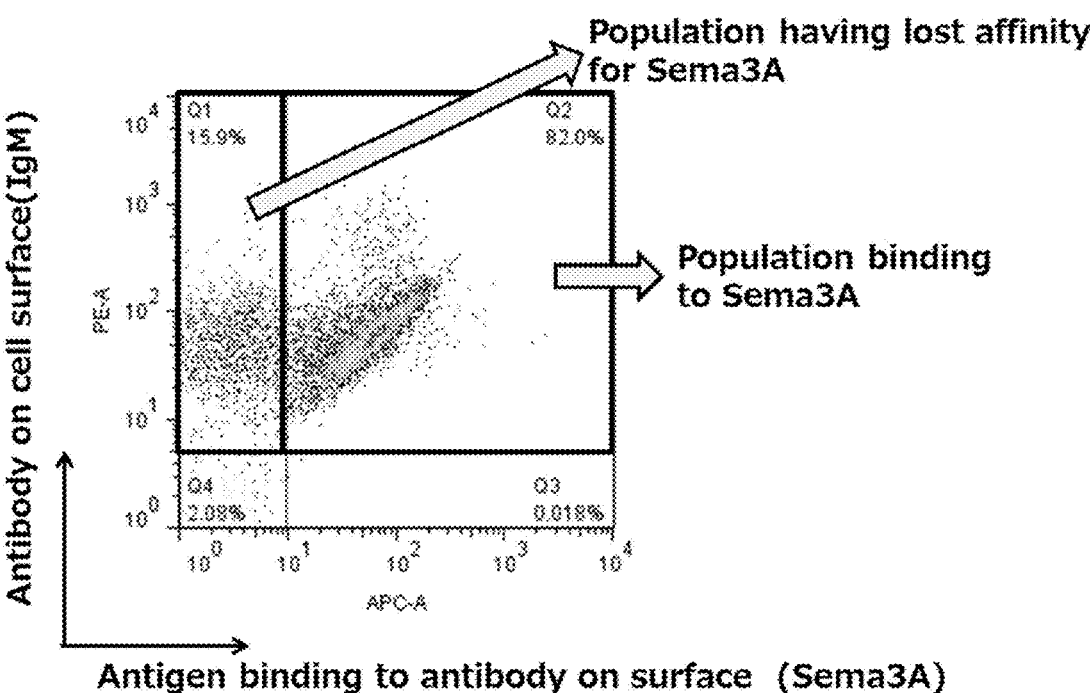
[Figure 2]
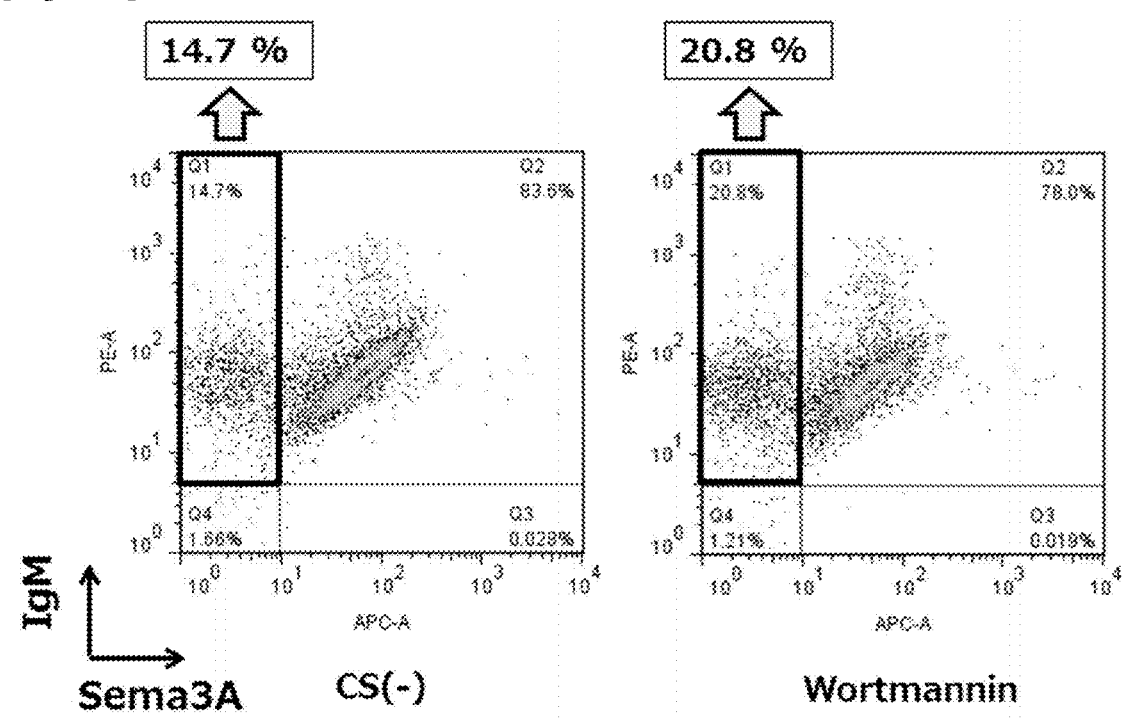

[Figure 3]
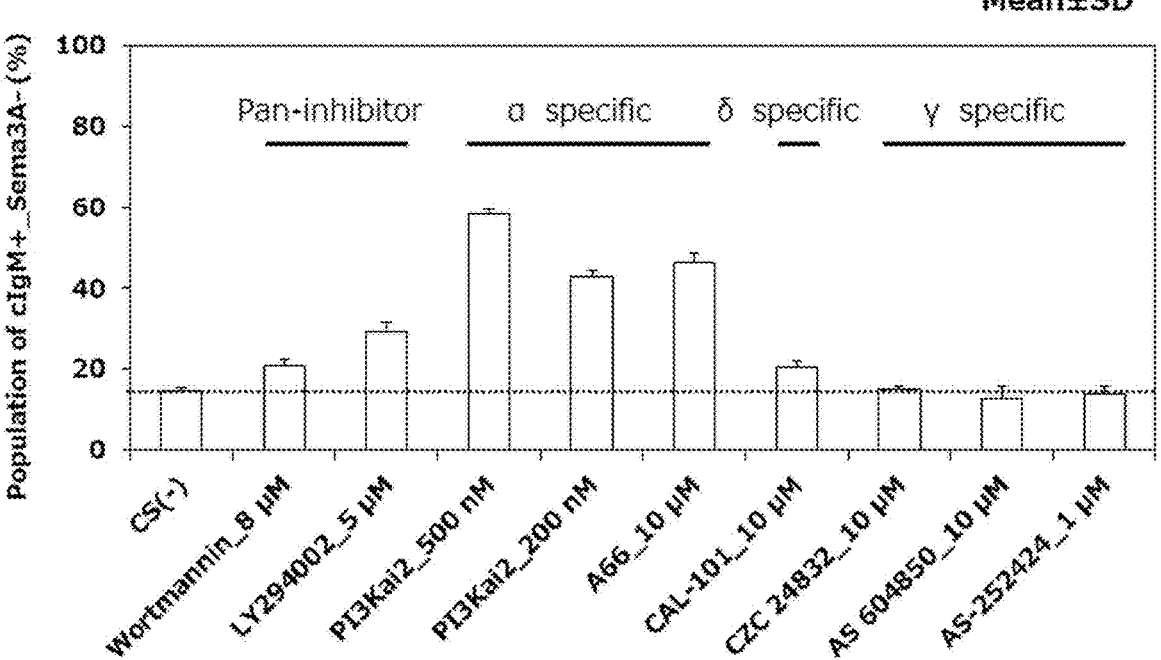
[Figure 4]
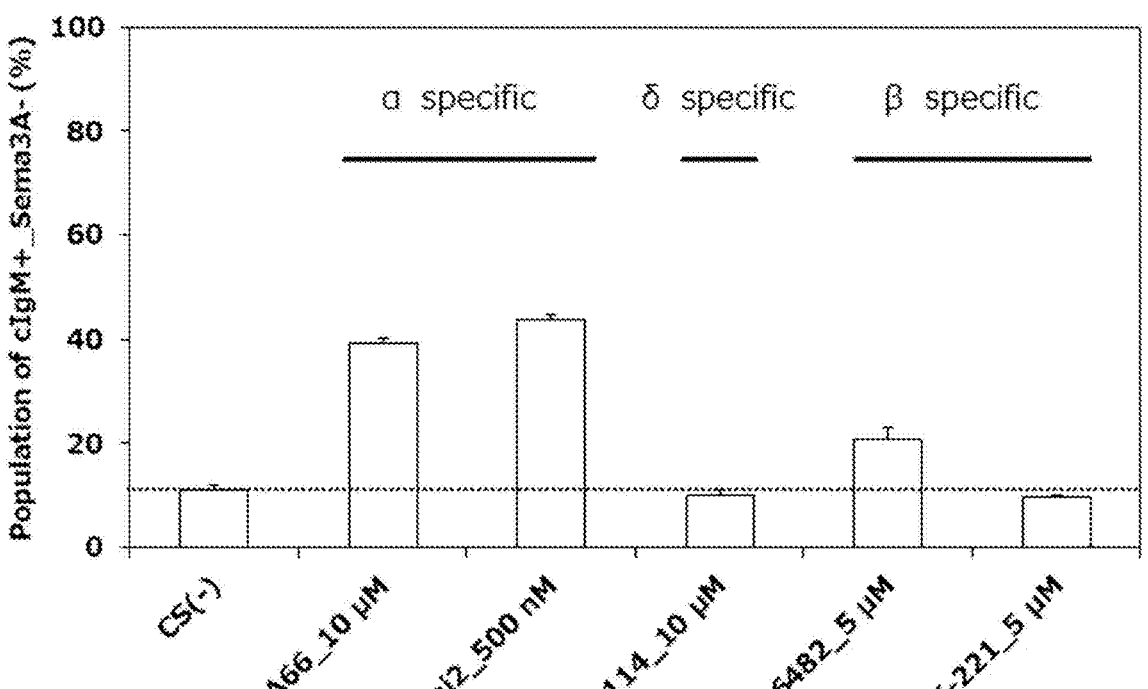

[Figure 5]
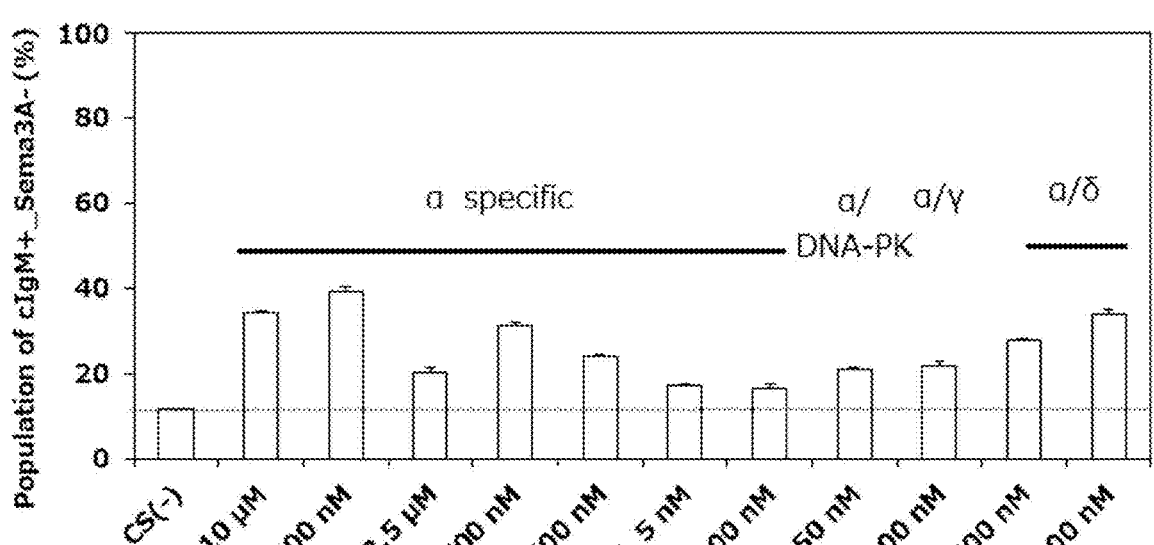
[Figure 6]
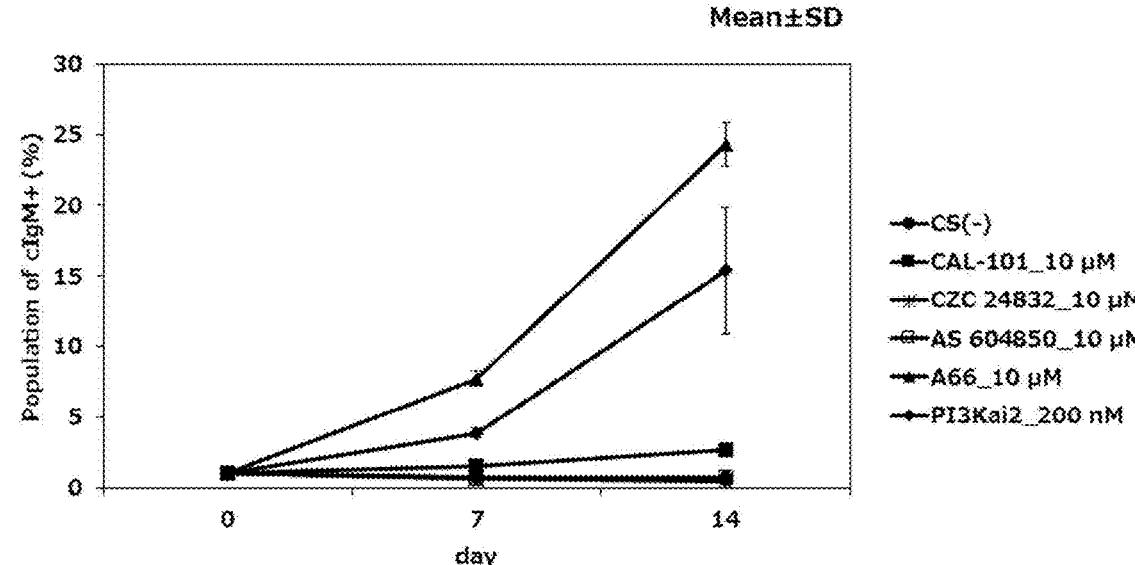

[Figure 7]
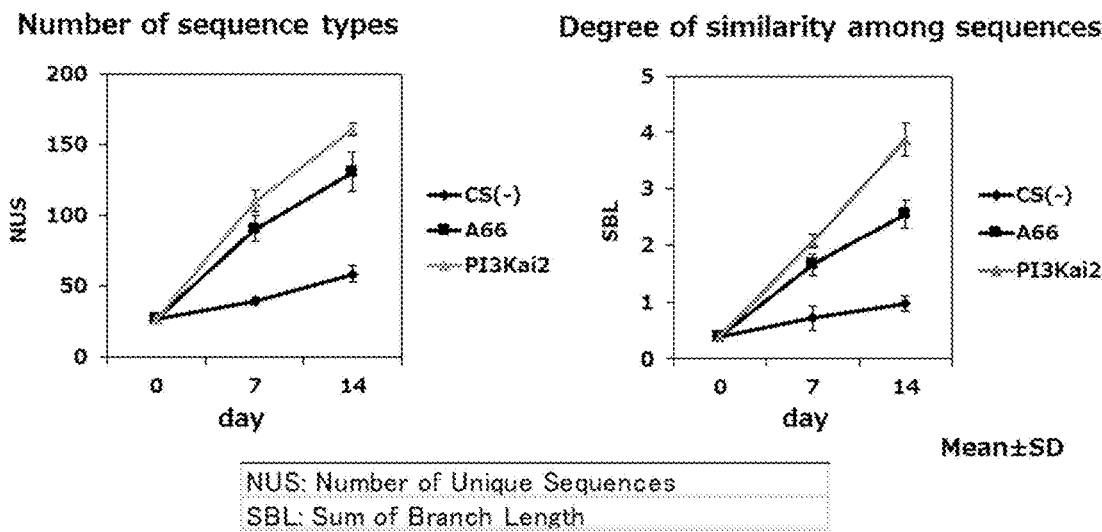
[Figure 8]
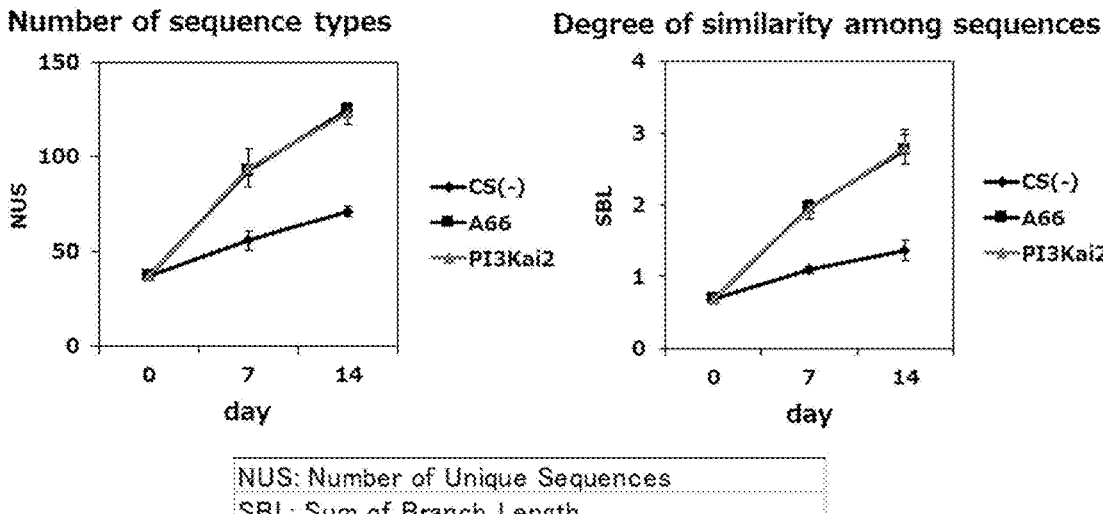

[Figure 9]
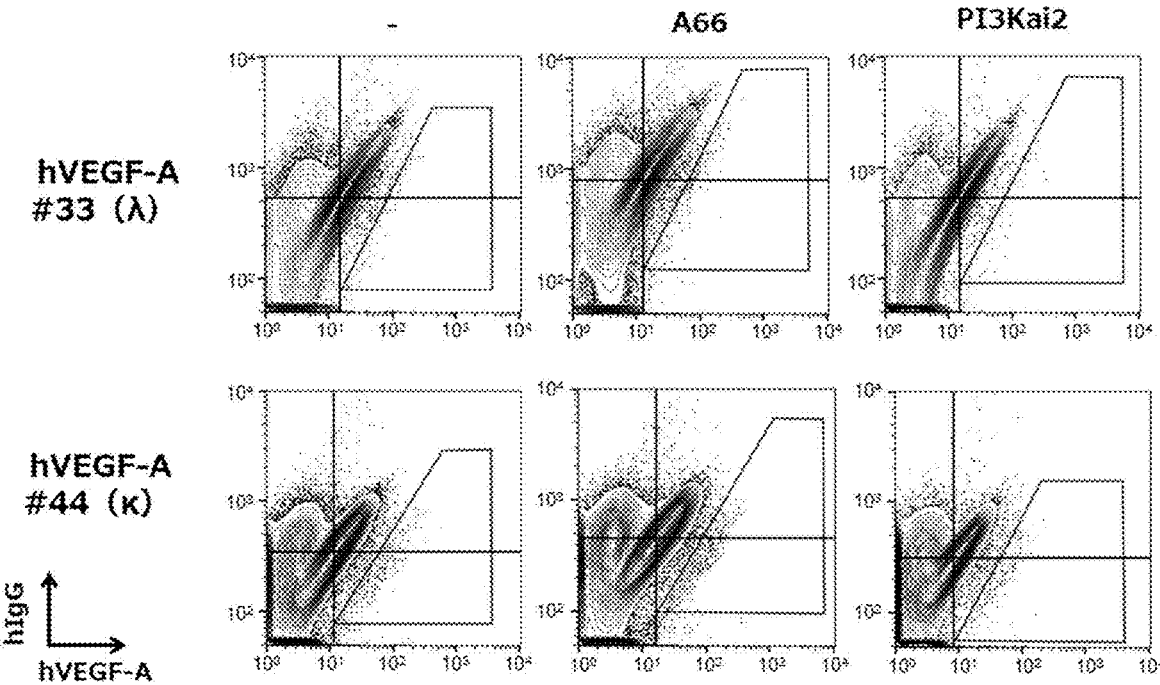
[Figure 10]
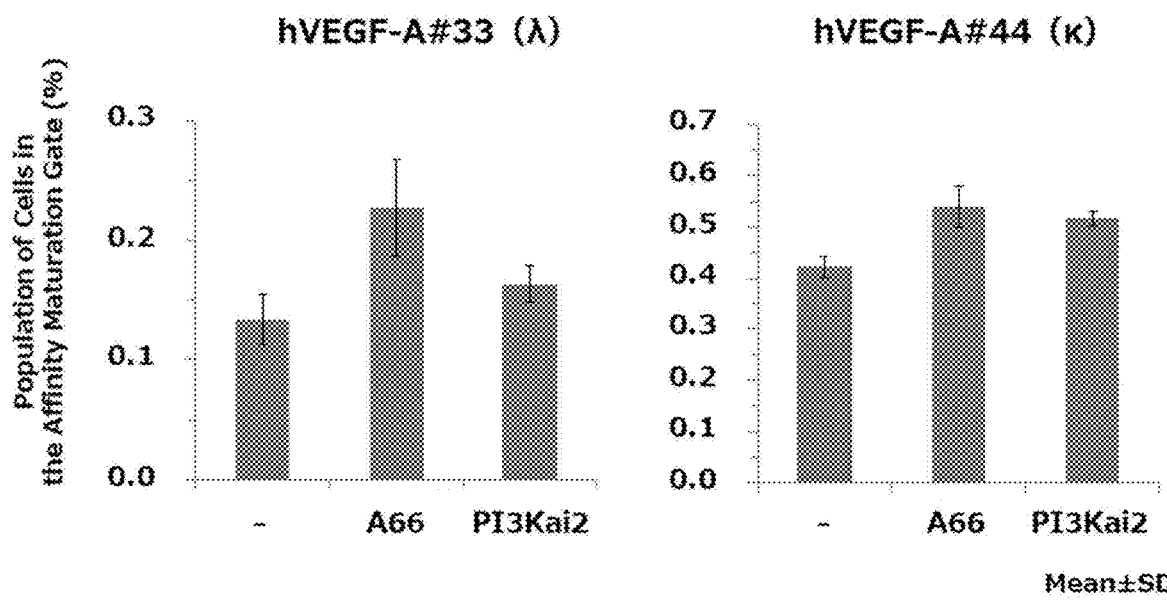

METHOD FOR PROMOTING DIVERSIFICATION OF ANTIBODY VARIABLE REGION

CROSS REFERENCE TO RELATED APPLICATIONS

This application is a continuation of U.S. patent application Ser. No. 16/484,061, filed Aug. 6, 2019, which is the U.S. National Phase Application of PCT International Application Number PCT/JP2018/004697, filed on Feb. 9, 2018, designating the United States of America and published in the Japanese language, which is an International Application of and claims the benefit of priority to Japanese Patent Application No. 2017-023001, filed on Feb. 10, 2017. The disclosures of the above-referenced applications are hereby expressly incorporated by reference in their entireties.

REFERENCE TO SEQUENCE LISTING

A Sequence Listing submitted as an ASCII text file via Patent Center is hereby incorporated by reference in accordance with 35 U.S.C. § 1.52(e). The name of the ASCII xml file for the Sequence Listing is SEQLISTING_WNGR001.002APC.xml, the date of creation of the ASCII text file is Jan. 2, 2023, and the size of the ASCII xml file is 21,653 bytes.

TECHNICAL FIELD

The present invention relates to a method for promoting diversification of the variable regions of an antibody.

BACKGROUND ART

An antibody binds to a specific antigen in a living body and provokes various biological defense reactions. Utilizing such properties of an antibody, various antibody drugs have been developed. In order to develop such antibody drugs, a technique of producing many types of antibodies, which bind with desired affinity to various antigens, is required.

In general, antibody production methods are classified into methods of utilizing animal immunization and methods of not utilizing animal immunization. As a method of utilizing animal immunization, a hybridoma method comprising immunizing an animal with an antigen and then fusing the obtained B cells with myelomas has been applied, for example. However, this method has been problematic in that time and effort are required to obtain an antibody because animals are used, and in that an antibody may not be obtained due to immune tolerance. As a method of not utilizing animal immunization, a phage display method has been applied, for example. This is a method comprising presenting a single chain antibody consisting of an antibody variable region (single chain variable fragment; scFv) to phage particles to obtain a clone binding to a target antigen. However, this method has been problematic in that the quality of a library depends on the diversity of scFv, and in that changes are generated in specificity or affinity in the process of converting scFv to a full-length antibody.

In addition to the above-described techniques of producing antibodies, a technique of producing antibodies by utilizing a chicken B cell-derived DT40 cell line, ADLib (registered trademark) System, has been developed, and it has become possible to utilize a library capable of generating human antibodies according to gene transfer (Patent Literatures 1, 2 and 3, and Non Patent Literature 1). Since a clone having an antibody specifically binding to an antigen can be selected from a library according to this system, immune tolerance can be avoided, and a full-length antibody can be promptly obtained. What is more, since the mechanism of the diversification of antibody variable regions, which is important for recognition of antigens, is gene conversion (GC), differing from V(D)J recombination in mice or humans, this system is advantageous in that changes in antibody gene sequences can be expected according to a mechanism different from antibodies produced in the living bodies of mice or humans.

Several methods for diversifying the sequences of variable region genes of an antibody have been reported so far. Examples of such a method include: animal immunization of using GANP mice (registered trademark), in which many somatic mutations are induced in the antibody variable regions of germinal center B cells, in comparison to normal wild-type mice (Patent Literature 4); and methods of utilizing avian B cells comprising an inactivated XRCC3 gene (Patent Literature 5), or avian B cells in which the expression of an AID gene has been controlled (Patent Literature 6), or a DT40-SWΔC cell line, into which mutant AID with enhanced AID activity associated with mutation introduction has been introduced (Non Patent Literature 2).

Among others, the AID (activation-induced deaminase) protein has an important function in causing somatic hypermutation (SHM) associated with the diversity of antibodies or maturation of affinity, class switch recombination (CSR) for changing the class of the constant region of an antibody, and gene conversion (GC), and thus, a large number of studies have been conducted regarding AID. When AID is associated with different phenomena such as somatic hypermutation or class switch recombination, what mechanism regulates the functions of the AID is an extremely interesting issue. As a result of an experiment using AID mutants, it has been reported that the C-terminus of AID is important for class switch recombination but is not necessary for somatic hypermutation or gene conversion (GC) (Non Patent Literature 3). Moreover, it has been suggested that different factors be recruited by AID, and then, the recruited factors induce different phenomena such as class switch recombination or somatic hypermutation (Non Patent Literature 4).

PI3 Kinase (phosphoinositide 3-kinase: PI3K) has been known as a factor functioning upstream of AID. PI3 Kinase phosphorylates the position 3 of the inositol ring of phosphatidylinositol, and plays an important role in various cellular functions such as cell survival, cell growth, cell motility, and the transport of intracellular organelle. Such PI3 kinase is classified into three classes (i.e., classes I, II, and III) in terms of structure. Class I is further divided into classes IA and IB, and of these, regarding the class IA, three isotypes p110α, p110β and p110δ have been known as catalytic subunits.

With regard to the relationship of PI3K with AID, as a result of studies using a PI3K inhibitor in mouse B cells, it has been demonstrated that when p110δ signaling is suppressed, the expression of AID is increased and class switch recombination is promoted (Non Patent Literature 5 and Non Patent Literature 6).

As described above, various factors are complicatedly involved in the diversification of the variable region genes of an antibody, and the control mechanism thereof still remains unknown in many respects.

CITATION LIST

Patent Literature

Patent Literature 1: Japanese Patent No. 4214234
Patent Literature 2: WO2008/047480
Patent Literature 3: WO2015/167011
Patent Literature 4: Japanese Patent No. 4478577
Patent Literature 5: JP Patent Publication (Kokai) No. 2009-060850 A
Patent Literature 6: JP Patent Publication (Kokai) No. 2006-109711 A
Non Patent Literature 1: Seo et al., Nature Biotechnol. 23, 731-735 2005
Non Patent Literature 2: Yuichi KANEHIRO et al., Summary of Annual Meeting of the Society for Biotechnology, Japan, p. 109, 2008
Non Patent Literature 3: Barreto et al., Mol. Cell 12, 501-508, 2003
Non Patent Literature 4: Heltemes-Harris et al., Mol Immuno. 45, 1799-1806, 2008
Non Patent Literature 5: Omori et al., Immunity 25, 545-557, 2006
Non Patent Literature 6: Zhang et al., J Immunol. 191, 1692-1703, 2013
Non Patent Literature 7: Backer, Curr Top Microbiol Immunol. 346, 87-114, 2010

SUMMARY OF INVENTION

Technical Problem

Taking into consideration the above-described circumstances, it is an object of the present invention to provide a method for promoting diversification of the amino acid sequences of antibody variable regions and/or the gene sequences of antibody variable regions, which are generated by an avian B cell population.

Solution to Problem

The present inventors have screened for a drug for diversifying the amino acid sequences (complementarity-determining regions (CDR 1-3)) and a framework region (FR) of antibody variable regions (heavy chain (H chain) and light chain (L chain)). As a result, the present inventors have found that an inhibitor specific to the p110α isotype of a PI3 kinase catalytic subunit (hereinafter referred to as "PI3Kα") is effective for the diversification of the amino acid sequences of antibody variable regions. As mentioned above, it had been reported that, in mouse B cells, an inhibitor specific to the p110δ isotype (hereinafter referred to as "PI3Kδ") promotes class switch recombination. However, the present inventors have confirmed that the inhibitor to PI3Kδ hardly had influence on the diversification of the amino acid sequences of antibody variable regions of avian B cells.

In view of the above, it has been suggested that signals from PIK3α and PIK3δ are likely to be associated with the diversification of the antibody variable regions and class switch recombination in antibody constant regions, in each different pathways, or in collaboration with different factors, or that pathways for inducing changes to the antibody sequences of B cells are different between mice and birds.

The present invention has been completed based on the aforementioned findings.

Specifically, the present invention includes the following (1) to (9).

(1) A method for promoting diversification of the amino acid sequences of variable regions of an antibody generated by an avian B cell population, wherein the method comprises suppressing the PI3Kα activity of each avian B cell comprised in the avian B cell population expressing the antibody.

(2) The method according to the above (1), which is characterized in that the avian B cell is a chicken B cell.

(3) The method according to the above (2), which is characterized in that the chicken B cell is a DT40 cell.

(4) The method according to any one of the above (1) to (3), which is characterized in that the antibody variable region is an antibody heavy chain variable region.

(5) The method according to any one of the above (1) to (3), which is characterized in that the antibody variable region is an antibody light chain variable region.

(6) The method according to any one of the above (1) to (5), which is characterized in that the suppression of the PI3Kα activity is induced by allowing a PI3Kα-specific inhibitor to come into contact with the avian B cell.

(7) The method according to the above (6), which is characterized in that the PI3Kα-specific inhibitor is any one of PI3Kα Inhibitor 2 and A66.

(8) The method according to any one of the above (1) to (7), which is characterized in that the antibody expressed by the avian B cell is IgM or IgG.

(9) The method according to any one of the above (1) to (8), which is characterized in that the antibody expressed by the avian B cell is an avian antibody, a chimeric antibody, a humanized antibody, or a human antibody.

Advantageous Effects of Invention

According to the method of the present invention, it becomes possible to promote diversification of the amino acid sequences of variable regions of an antibody generated by an avian B cell population, and thus, an antibody reacting against a desired antigen can be easily prepared.

BRIEF DESCRIPTION OF DRAWINGS

FIG. 1 shows a summary of a method for evaluating the diversification of antibody variable regions according to flow cytometry.

FIG. 2 shows an example of analyzing antibody variable regions using the PI3K inhibitor Wortmannin. "CS(−)" indicates an example of performing the analysis under drug non-additive conditions.

FIG. 3 shows comparison (1) in terms of the effects of PI3K inhibitors having different specificity on the diversification of antibody variable regions. As such inhibitors, Pan-inhibitors (exhibiting inhibitory effects on all of PI3Kα, β, δ and γ), PI3Kα-specific inhibitors, a PI3Kδ-specific inhibitor, and PI3Kγ-specific inhibitors were used. The longitudinal axis indicates the percentage of cIgM+_Sema3A− cells.

FIG. 4 shows comparison (2) in terms of the effects of PI3K inhibitors having different specificity on the diversification of antibody variable regions. As such inhibitors, PI3Kα-specific inhibitors, a PI3Kδ-specific inhibitor, and PI3Kβ-specific inhibitors were used. The longitudinal axis indicates the percentage of cIgM+_Sema3A− cells.

FIG. 5 shows a comparison in terms of the effects of PI3Kα inhibitors on the diversification of antibody variable regions. As such inhibitors, PI3Kα-specific inhibitors and drugs having PI3Kα inhibitory activity were used. The longitudinal axis indicates the percentage of cIgM+ _Sema3A– cells.

FIG. 6 shows the verification results of light chain GC according to Reversion assay. "CS(–)" indicates a drug non-additive control. CAL-101: PI3Kδ-specific inhibitor, CZC 24832: PI3Kγ-specific inhibitor, AS 604850: PI3Kγ-specific inhibitor, A66: PI3Kα-specific inhibitor, and PI3Kai2 (PI3Kα Inhibitor 2): PI3Kα-specific inhibitor.

FIG. 7 shows the diversity analysis results of the amino acid sequences of antibody heavy chain variable regions according to NGS analysis.

FIG. 8 shows the diversity analysis results of the amino acid sequences of antibody light chain variable regions according to NGS analysis.

FIG. 9 shows an example of analyzing cell groups, the antigen-binding ability of which has been improved as a result of Affinity Maturation. The symbol "–": drug non-additive conditions, A66: conditions comprising PI3Kα-specific inhibitor A66, and PI3Kai2: conditions comprising PI3Kα-specific inhibitor PI3Kα Inhibitor 2.

FIG. 10 shows the percentage of cells, the antigen-binding ability of which has been improved as a result of Affinity Maturation. The symbol "–": drug non-additive conditions, A66: conditions comprising PI3Kα-specific inhibitor A66, and PI3Kai2: conditions comprising PI3Kα-specific inhibitor PI3Kα Inhibitor 2.

DESCRIPTION OF EMBODIMENTS

An embodiment of the present invention relates to a method of suppressing the PI3Kα activity of individual avian B cells comprised in an avian B cell population that expresses antibodies, so as to promote diversification of the amino acid sequences of variable regions of antibodies (antibody group) generated by the avian B cell population.

The term "avian B cells" in the phrase "avian B cell population (a plurality of avian B cells)" used in the present embodiment means avian B cells that generate antibodies. The avian B cells may be, for example, DT 40 cells as a chicken B cell-derived cell line, but are not particularly limited thereto. Moreover, examples of the avian B cells also include avian B cells, on which a treatment of introducing a variety of mutations has been performed, such as avian B cells, in which an XRCC3 gene has been inactivated (JP Patent Publication (Kokai) No. 2009-060850 A), avian B cells, in which the expression of an AID gene has been controlled (JP Patent Publication (Kokai) No. 2006-109711 A), avian B cells, in which an antibody sequence has been diversified using a HDAC (Histone Deacetylase) inhibitor comprising TSA (Trichostatin A), and avian B cells, in which a foreign gene sequence or a portion thereof has been introduced onto the chromosome thereof (e.g., avian B cells, into which any given antibody gene sequence, etc. has been introduced).

The culture, etc. of the "avian B cells" used in the present embodiment can be easily carried out according to a method well known to a person skilled in the art, and thus, the culture conditions, etc. are not particularly limited. For example, in a case where the avian B cells are DT40 cells, IMDM medium (Invitrogen), etc. may be used, and the cells may be cultured in the presence of about 5% $CO_2$ at approximately 39.5° C.

In addition, the above-described "avian B cell population" may also have been cultured, in advance, in the presence of a calcineurin inhibitor (for example, FK506, etc.) and avian serum, before it is allowed to come into contact with an antigen. Otherwise, after completion of Affinity Maturation (which means, in the present description, a method for producing a clone or a clone group, whose binding ability to an antigen is not only enhanced, but which has a change to improve the properties of an antibody, such as the improvement of physical properties), when the avian B cell population is allowed to come into contact with an antigen, it may be cultured in the presence of a calcineurin inhibitor (for example, FK506, etc.) and avian serum.

In the present embodiment, the "avian B cell population that generates antibodies" includes avian B cells generating membrane antibodies and secreted antibodies, and avian B cells generating membrane antibodies or secreted antibodies.

In the present embodiment, the "antibody which the avian B cells generate" may be an avian antibody, a chimeric antibody, a humanized antibody, or a human antibody. With regard to the shape of an antibody, a full-length antibody, an antibody fragment (for example, F(ab')2, Fab', Fab, Fv, scFv, Fc, etc.), and a protein comprising the amino acid sequences of the variable regions of the heavy chain and/or light chain of an antibody, can be used, but are not limited thereto. Moreover, the antibody may also be a multispecific antibody (for example, a bispecific antibody), an antibody fragment thereof, or the like.

In the present description, the chimeric antibody is an antibody formed by linking regions having different origins to each other, and examples of the chimeric antibody include an antibody formed by linking a variable region to a constant region, the origins of which are different from each other, and an antibody formed by linking a Fab region to a Fc region, the origins of which are different from each other, but are not limited thereto. For instance, a bird-mouse chimeric antibody is an antibody formed by linking the amino acid sequence of an avian gene-derived antibody to the amino acid sequence of a mouse gene-derived antibody. Other examples of the chimeric antibody include: a bird-human chimeric antibody formed by linking the amino acid sequence of an avian gene-derived antibody to the amino acid sequence of a human gene-derived antibody; a bird-rabbit chimeric antibody formed by linking the amino acid sequence of an avian gene-derived antibody to the amino acid sequence of a rabbit gene-derived antibody; and a bird-goat chimeric antibody formed by linking the amino acid sequence of an avian gene-derived antibody to the amino acid sequence of a goat gene-derived antibody.

The humanized antibody is an antibody, in which among the amino acid sequences of the heavy or light chains of a generated antibody, some sequences are avian gene-derived sequences, and other sequences are human gene-derived sequences. On the other hand, the human antibody is an antibody, in which all of the amino acid sequences of the heavy or light chains of a generated antibody are human gene-derived sequences.

Furthermore, in the present embodiment, the "antibody which the avian B cells generate" includes antibodies comprising the entire or a part of the amino acid sequences of antibodies derived from animal species other than birds. Specific examples include, but are not limited to, antibodies comprising the entire or a part of the amino acid sequences of antibodies obtained from a mouse, a rat, a rabbit, a bovine, a goat, and the like.

In the present embodiment, the isotypes of the "antibody which the avian B cells generate" are not particularly limited. Examples of such an isotype include IgM, IgG, IgA, and IgY.

In the present embodiment, the "variable region of an antibody" may be either the variable region of an antibody heavy chain (H chain) or the variable region of an antibody light chain (L chain). The variable region of an antibody is a region consisting of complementarity-determining regions (CDR 1-3) and a framework region (FR).

In the present embodiment, the "diversification" of the amino acid sequences of variable regions of an antibody means that, when the amino acid sequences of the variable regions of antibodies, which individual avian B cells constituting an avian B cell population generate, are compared with each other, the percentage of sequences identical to each other is decreased, and sequences different from each other (in particular, sequences having a low degree of similarity to each other) is increased. Examples of the indicator of the "diversification" of the amino acid sequences of variable regions that can be used herein may include, but are not particularly limited to, the antigen specificity of an antibody generated by the avian B cell population as a target, a change in antigen-binding ability, physical properties and the like, and the number of the types of the amino acid sequences of antibody variable regions and identity or homology among the sequences. Further, since the amino acid sequences of antibody variable regions are univocally determined by the DNA sequences thereof, the diversity thereof can also be determined using, as an indicator, the number of the types of the DNA sequences of the variable regions of antibodies generated by the avian B cell population as a target, identity or homology among the sequences, etc.

When the amino acid sequences of antibody variable regions of individual cells constituting the avian B cell population are diversified, changes are generated in the antigen specificity, affinity, physical properties and the like of antibodies generated by individual avian B cells, so that the diversification of antibodies obtained from the avian B cell population can be achieved.

The "PI3Kα" of the present embodiment means PI3 kinase catalytic subunit α isotype (p110α) (Non Patent Literature 7). Herein, examples of the method of suppressing the activity of PI3Kα may include, but are not limited to, a method of using a PI3Kα-specific activity inhibitor and a method of reducing or eliminating the function of a PI3KCA gene encoding PI3Kα.

The method of using a PI3Kα-specific activity inhibitor can be carried out, for example, by allowing a PI3Kα-specific inhibitor such as PI3Kα Inhibitor 2, A66, PF-4989216, INK1117, GSK1059615, GDC-0941, BYL719, PI-103, PIK-90, PIK-75 or HS-173 to come into contact with avian B cells, and thus treating the cells. The method of allowing the PI3Kα-specific inhibitor to come into contact with the avian B cells could be easily selected from known techniques by a person skilled in the art. For example, a method of culturing avian B cells in a state in which a PI3Kα-specific inhibitor is present in a medium may be applied. The concentration of the PI3Kα-specific inhibitor in the medium is different depending on the type of the inhibitor used. A person skilled in the art could easily determine the effective concentration of the PI3Kα-specific inhibitor within a range that does not damage the avian B cells, by performing preliminary experiments and the like. When the used PI3Kα-specific inhibitor is, for example, PI3Kα Inhibitor 2, the inhibitor may be added into a medium to a concentration of approximately 500 nM to 5 nM. Likewise, in the case of using A66, the concentration may be approximately 10 μM to 100 nM; in the case of using PF-4989216, the concentration may be approximately 500 nM to 50 nM; in the case of using INK1117, the concentration may be approximately 2.5 μM to 25 nM; in the case of using GSK1059615, the concentration may be approximately 500 nM to 5 nM; in the case of using GDC-0941, the concentration may be approximately 500 nM to 5 nM; in the case of using BYL719, the concentration may be approximately 500 nM to 5 nM; in the case of using PI-103, the concentration may be approximately 50 nM to 5 nM; in the case of using PIK-90, the concentration may be approximately 100 nM to 10 nM; in the case of using PIK-75, the concentration may be approximately 5 nM to 0.5 nM; and in the case of using HS-173, the concentration may be approximately 50 nM to 5 nM.

Moreover, the PI3Kα-specific inhibitor is not particularly limited, as long as it specifically inhibits the activity of PI3Kα. The PI3Kα-specific inhibitor may be any one of a low-molecular-weight compound, a protein, and a peptide, and also, a commercially available product can be purchased and used.

The time necessary for allowing the PI3Kα-specific inhibitor to come into contact with the avian B cells and treating the cells with the inhibitor is different, depending on the type of the inhibitor used and the concentration thereof. For example, when the above-described PI3Kα-specific inhibitor is used, the necessary time may be approximately 24 to 72 hours.

Examples of the method of reducing or eliminating the function of a PI3KCA gene may include a method of reducing or eliminating the activity of PI3Kα by performing genetic manipulation (e.g., introduction of point mutation, or mutation such as deletion, insertion or addition; and genome editing by knock-in, knock-out or CRISPER/Cas system) on a PI3KCA gene; a method of reducing or eliminating the expression of PI3Kα; and a method of reducing or eliminating the expression of PI3Kα, using shRNA, etc. (RNAi method).

The disclosures of all publications cited in the present description are incorporated herein by reference in their entirety. In addition, throughout the present description, when singular terms such as "a," "an," and "the" are used, these terms include not only single items but also multiple items, unless otherwise clearly specified.

Hereinafter, the present invention will be further described in the following examples. However, these examples are only illustrative examples of the embodiments of the present invention, and thus, are not intended to limit the scope of the present invention.

EXAMPLES

1. Materials and Methods 1-1. Test Subjects, Samples, and Used Materials
1-1-1. Cell Lines
In the present Examples, the chicken-derived B cell lines, DT40 cells, namely, a BMAA4-2 cell line (WO2014/123186), a CL18_M– cell line (the CL18 cell line used in the present Examples; Buerstedde et al., EMBO J. 9, 921-927, 1990), an hVEGF-A #33 cell line, and an hVEGF-A #44 cell line were used. The BMAA4-2 cell line includes cells generating an anti-Sema3A antibody (chicken IgM: cIgM), the hVEGF-A #33 cell line and the hVEGF-A #44 cell line include cells generating an anti-hVEGF antibody (human IgG: hIgG), and the CL18_M– cell line has a frame shift in the cIgM antibody gene region thereof, and thus, in general, does not generate the cIgM antibody.

The BMAA4-2 cell line was produced according to the method described in WO2014/123186. The hVEGF-A #33 cell line and the hVEGF-A #44 cell line were selected from a human ADLib library (a library modified in accordance with the method described in WO2015/167011), using human VEGF-A (hereinafter referred to as "hVEGF-A") as an antigen, and were each isolated as clones specifically binding to hVEGF-A. The hVEGF-A #33 cell line has a light chain λ chain, whereas the hVEGF-A #44 cell line has a light chain κ chain. These are cell lines generating antibodies derived from different antibody gene sequences.

1-1-2. Medium, Serums, Antibiotic, Etc.

For the culture of DT40 cells, Iscove' s Modified Dulbecco' s Medium (IMDM, Gibco, 12440079) was used as a medium, and as serums, Fetal Bovine Serum (FBS, Biosera, FB1280/500, lot. 11824) and Chicken Serum (CS, Gibco, 16110082, lot. 1383279) were used. Also, as an antibiotic, Penicillin-Streptomycin Mixed Solution (Stabilized) (P/S, Nacalai Tesque, 09367-34) was used. In addition, after completion of Affinity Maturation, FK-506 (Cayman, 10007965) was added and used.

1-1-3. Antigens and Antibodies

As antigens used in analyzing the diversification of antibodies, a cynomolgus monkey Sema3A protein fused with a His tag and an AP tag (His-AP-cySema3A, NCBI Reference Sequence: XP_005550410.1) and an hVEGF-A protein fused with a FLAG tag (27-191 amino acid sequence, UniProt #P15692-4) were prepared. Antibodies used in the analysis were Mouse Anti-Chicken IgM-PE (SouthernBiotech, 8310-09), Goat anti-Chicken IgM Antibody FITC Conjugated (Bethyl, A30-102F), and Goat Anti-Human IgG-PE (SouthernBiotech, 2040-09).

1-1-4. Primers Used in Next-Generation Sequencing (Ngs) Analysis

---

Analysis of DNA sequences of antibody heavy chain variable regions

BHcF1;
5'-CTATGCGCCTTGCCAGCCCGCTCAGCGCTCTCTGCCCTTCC-3'
(SEQ ID NO: 1)

A001HcR;
5'-CGTATCGCCTCCCTCGCGCCATCAGACGAGTGCGTCGATGACTTCGGTCCCGTG-3'
(SEQ ID NO: 2)

A002HcR;
5'-CGTATCGCCTCCCTCGCGCCATCAGACGCTCGACACGATGACTTCGGTCCCGTG-3'
(SEQ ID NO: 3)

A003HcR;
5'-CGTATCGCCTCCCTCGCGCCATCAGAGACGCACTCGATGACTTCGGTCCCGTG-3'
(SEQ ID NO: 4)

A004HcR;
5'-CGTATCGCCTCCCTCGCGCCATCAGAGCACTGTAGCGATGACTTCGGTCCCGTG-3'
(SEQ ID NO: 5)

A005HcR;
5'-CGTATCGCCTCCCTCGCGCCATCAGATCAGACACGCGATGACTTCGGTCCCGTG-3'
(SEQ ID NO: 6)

A006HcR;
5'-CGTATCGCCTCCCTCGCGCCATCAGATATCGCGAGCGATGACTTCGGTCCCGTG-3'
(SEQ ID NO: 7)

A007HcR;
5'-CGTATCGCCTCCCTCGCGCCATCAGCGTGTCTCTACGATGACTTCGGTCCCGTG-3'
(SEQ ID NO: 8)

---

Analysis of DNA sequences of antibody light chain variable regions

A001NGSLCF;
5'-CGTATCGCCTCCCTCGCGCCATCAGACGAGTGCGTCAGGTTCCCTGGTGCAGGC-3'
(SEQ ID NO: 9)

-continued

```
A002NGSLCF;
5'-
CGTATCGCCTCCCTCGCGCCATCAGACGCTCGACACAGGTTCCCTGGTGCAGGC-
3'
(SEQ ID NO: 10)

A003NGSLCF;
5'-
CGTATCGCCTCCCTCGCGCCATCAGAGACGCACTCAGGTTCCCTGGTGCAGGC-3'
(SEQ ID NO: 11)

A005NGSLCF;
5'-
CGTATCGCCTCCCTCGCGCCATCAGATCAGACACGCAGGTTCCCTGGTGCAGGC-
3'
(SEQ ID NO: 12)

A006NGSLCF;
5'-
CGTATCGCCTCCCTCGCGCCATCAGATATCGCGAGCAGGTTCCCTGGTGCAGGC-
3'
(SEQ ID NO: 13)

A007NGSLCF;
5'-
CGTATCGCCTCCCTCGCGCCATCAGCGTGTCTCTACAGGTTCCCTGGTGCAGGC-
3'
(SEQ ID NO: 14)

A012NGSLCF;
5'-
CGTATCGCCTCCCTCGCGCCATCAGCGAGAGATACAGGTTCCCTGGTGCAGGC-3'
(SEQ ID NO: 15)

cmNGSLcR-3B;
5'-CTATGCGCCTTGCCAGCCCGCTCAGATGTCACAATTTCACGATGG-3'
(SEQ ID NO: 16)
```

1-1-5. Reagents, Etc.

In the present Examples, the reagents shown in Table 1 to Table 3 were used.

TABLE 1

List of Screened Drugs

| Drug Name | Function | Company name, Catalog No. |
|---|---|---|
| T2AA | mono-ubiquitinated PCNA inhibition | Sigma-Aldrich, SML0794 |
| RI-1 | RAD51 inhibition | Abeam, ab144558 |
| B02 | RAD51 inhibition | Merk/Millipore, 553525 |
| Piperlongumine | ROS increase | Sigma-Aldrich, SML0221 |
| Irinotecan | TopoisomeraseI inhibition | Cayman chemical, 14180 |
| Etoposide | TopoisomeraseII inhibition | Cayman chemical, 12092 |
| Lipopoly-saccharides from *Escherichia coli* O111:B4 | TLR4 ligand | Sigma-Aldrich, L3024 |
| Poly(I:C) | TLR3 ligand | InvivoGen, tlrl-pic |
| ODN D-SL01 | TLR9 ligand | InvivoGen, tlrk-dsl01 |
| Chicken CD40LG Recombinant Protein | CD40 ligand | ImmunoChemistry Technologies, 6602 |
| Chicken BAFF Recombinant Protein | B-cell activation factor | ImmunoChemistry Technologies, 6554 |
| Fluocinonide | Glucocorticoid | Santa Cruz, sc-255177 |
| Wortmannin | PI3K inhibition | Cayman chemical, 10010591 |
| Rapamycin | FKBP-12 inhibition | Cayman chemical, 13346 |
| Calcitriol | Vitamin D3 analog | Cayman chemical, 71820 |

TABLE 1-continued

List of Screened Drugs

| Drug Name | Function | Company name, Catalog No. |
|---|---|---|
| Methotrexate | Dihydrofolate reductase (DHFR) inhibition | Cayman chemical, 13960 |
| 10058-F4 | c-Myc-Max dimerization inhibition | Cayman chemical, 15929 |
| CPI-203 | Bromodomain-containing protein 4 (BRD4) inhibition | Cayman chemical, 15479 |
| PF-04691502 | mTOR/PI3K inhibition | Sigma-Aldrich, PZ0235 |
| PF-05212384 | mTOR/PI3K inhibition | Sigma-Aldrich, PZ0281 |
| SCR7 pyrazine | DNA ligase IV inhibition | Cayman chemical, 18015 |
| Cdk2 Inhibitor II | Cdk2 inhibition | Cayman chemical, 15154 |
| Cdk4 Inhibitor | Cdk4 inhibition | Cayman chemical, 17648 |
| Cdk1/5 Inhibitor | Cdk1/5 inhibition | Cayman chemical, 18740 |
| Cdk1/2 Inhibitor III | Cdk1/2 inhibition | Cayman chemical, 18859 |
| Cdk4/6 Inhibitor IV | Cdk4/6 inhibition | Cayman chemical, 17974 |

TABLE 2

PI3K Inhibitor

| Drug Name | Function | Company name, Catalog No. |
|---|---|---|
| Wortmannin | PI3K inhibition | Cayman chemical, 10010591 |
| LY294002 | PI3K inhibition | Cayman chemical, 70920 |

TABLE 2-continued

| PI3K Inhibitor | | |
| --- | --- | --- |
| Drug Name | Function | Company name, Catalog No. |
| A66 | PI3Kα inhibition | Sigma-Aldrich, SML1213 |
| PI3Kα Inhibitor 2 | PI3Kα inhibition | Cayman chemical, 10010177 |
| INK1117 (MLN1117) | PI3Kα inhibition | Cayman chemical, 19514 |
| GSK1059615 | PI3Kα inhibition | Cayman chemical, 11569 |
| BYL719 | PI3Kα inhibition | Cayman chemical, 16986 |
| PIK-75 | PI3Kα inhibition | Cayman chemical, 10009210 |
| HS-173 | PI3Kα inhibition | Cayman chemical, 19156 |
| PI-103 | PI3Kα/DNA-PK inhibition | Cayman chemical, 10009209 |
| PIK-90 | PI3Kα/γ inhibition | Cayman chemical, 10010749 |
| PF-4989216 | PI3Kα/δ inhibition | Cayman chemical, 19308 |
| GDC-0941 | PI3Kα/δ inhibition | Cayman chemical, 11600 |
| AZD6482 | PI3Kβ inhibition | Cayman chemical, 15250 |
| TGX-221 | PI3Kβ inhibition | Cayman chemical, 10007349 |
| CZC 24832 | PI3Kγ inhibition | Sigma-Aldrich, SML1214 |
| AS 604850 | PI3Kγ inhibition | Sigma-Aldrich, A0231 |
| AS-252424 | PI3Kγ inhibition | Sigma-Aldrich, A8981 |
| CAL-101 | PI3Kδ inhibition | Cayman chemical, 15279 |
| IC-87114 | PI3Kδ inhibition | Cayman chemical, 11589 |

TABLE 3

| List of screened Drugs Used in Human Antibody Producing Cell Lines | | |
| --- | --- | --- |
| Drug Name | Function | Company name, Catalog No. |
| T2AA | mono-ubiquitinated PCNA inhibition | Sigma-Aldrich, SML0794 |
| Wortmannin | PI3K inhibition | Cayman chemical, 10010591 |
| A66 | PI3Kα inhibition | Sigma-Aldrich, SML1213 |
| AS-252424 | PI3Kγ inhibition | Sigma-Aldrich, A8981 |
| IC-87114 | PI3Kδ inhibition | Cayman chemical, 11589 |
| INK1117 | PI3Kα inhibition | Cayman chemical, 19514 |
| PI-103 | PI3Kα/DNA-PK inhibition | Cayman chemical, 10009209 |
| RI-1 | RAD51 inhibition | Abeam, ab144558 |
| Irinotecan | TopoisomeraseI inhibition | Cayman chemical, 14180 |
| CZC 24832 | PI3Kγ inhibition | Sigma-Aldrich, SML1214 |
| PIK-93 | PI4KIIIβ inhibition | Sigma-Aldrich, SML0546 |
| AZD6482 | PI3Kβ inhibition | Cayman chemical, 15250 |
| GSK1059615 | PI3Kα inhibition | Cayman chemical, 11569 |
| PIK-90 | PI3Kα/γ inhibition | Cayman chemical, 10010749 |
| B02 | RAD51 inhibition | Merk/Millipore, 553525 |
| LY294002 | PI3K inhibition | Cayman chemical, 70920 |
| AS 604850 | PI3Kγ inhibition | Sigma-Aldrich, A0231 |
| Calcitriol | Vitamin D3 analog | Cayman chemical, 71820 |
| TGX-221 | PI3Kβ inhibition | Cayman chemical, 10007349 |
| GDC-0941 | PI3Kα/δ inhibition | Cayman chemical, 11600 |
| PIK-75 | PI3Kα inhibition | Cayman chemical, 10009210 |
| Piperlongumine | ROS increase | Sigma-Aldrich, SML0221 |
| CAL-101 | PI3Kδ inhibition | Cayman chemical, 15279 |
| PI3Kα Inhibitor 2 | PI3Kα inhibition | Cayman chemical, 10010177 |
| PF-4989216 | PI3Kα/δ inhibition | Cayman chemical, 19308 |
| BYL719 | PI3Kα inhibition | Cayman chemical, 16986 |
| HS-173 | PI3Kα inhibition | Cayman chemical, 19156 |

1-2. Experimental Method

1-2-1. Composition of Media and Buffer

The following media and buffer were used.

(i) CS(−) medium

IMDM: 1,000 mL

FBS: 90 mL

P/S: 10 mL (ii) CS(+) medium

IMDM: 1,000 mL

FBS: 90 mL

P/S: 10 mL

CS: 10 mL (iii) FACS buffer

BSA: 5 g 0.5 M EDTA (pH 8.0): 4 mL

Phosphate Buffered Saline Powder: 1 unit $dH_2O$: 1,000 mL 0.22 µm Filter System (Corning, 431098).

1-2-2. Labeling of Antigen with Alexa Fluor 647 (Af647)

Using Alexa Fluor 647 Microscale Protein Labeling kit (Molecular probes, A30009), His-AP-cySema3A was labeled with AF647. Since the concentration of the protein used herein, His-AP-cySema3A, was less than 1 mg/mL (i.e., 0.626 mg/mL), the dye: molar ratios (MR) were set at 25, and the amount of the dye was calculated. Regarding other points, the instruction manuals included with the kit were applied. Using NanoDrop 2000c (ThermoFisher Scientific), A280 and A650 were measured, and the concentration of the protein in the fluorescently labeled sample was then determined. The thus produced AF647-labeled Sema3A was used in the subsequent experiments.

1-2-3. Sequence Change Analysis Using Bmaa4-2 Cell Line According to Flow Cytometry (Fcm)

A frozen stock of the BMAA4-2 cell line ($3.0 \times 10^6$ cells) was awaken with 10 mL of CS(−) medium, using a 25 cm² Flask (Corning, 430639), and the cells were then cultured in a $CO_2$ incubator (SANYO $CO_2$ Incubator MCO-20AIC, 39.5° C., 5% $CO_2$). On the following day, 500 µL each of a CS(−) medium, to which each drug had been added, was added into each well of a 48-well dish (Nunc, 150687), and the cells were then seeded thereon to a cell density of $6.0 \times 10^4$ cells/mL (wherein the cell concentration and the survival rate were measured using CASY cell counter (Nepa Gene)). After individual samples had been cultured for 2 days, the samples were subcultured under the same conditions to result in a cell density of $1.0 \times 10^4$ cells/mL. After completion of the culture for 3 days, individual samples were subcultured under the same conditions to result in a cell density of $6.0 \times 10^4$ cells/mL. After completion of the culture for 2 days (Day 7 of the culture), individual samples (in each amount of $2.0 \times 10^5$ cells) were transferred into each well of a 96-well plate (Nunc, 249662), and thereafter, a supernatant was removed by centrifugation at 300× g for 5 min. 200 µL each of FACS buffer was added into each well, and the cells were washed. After that, the resulting cells were centrifuged (300× g, 3 min) again, and a supernatant was then removed. This washing step was carried out repeatedly twice, and each sample was then suspended in 50 µL of FACS buffer comprising AF647-labeled Sema3A (5 nM) and 200-fold diluted Mouse Anti-Chicken IgM-PE. The light was shielded, and the obtained suspension was then reacted at 4° C. for 30 min. After completion of the staining, the reaction mixture was washed with a FACS buffer twice, and each sample was then suspended in 100 µL of FACS buffer comprising 1,000-fold diluted 7-AAD (BD Pharmingen, 559925), followed by measurement using FACS Canto II Flow Cytometer. Using FSC-SSC plot, dead cells, doublet cells, and 7-AAD-positive cells were removed. Thereafter, a plot, in which the vertical axis indicated APC (AF647-labeled Sema3A) and the longitudinal axis indicated PE (Mouse Anti-Chicken IgM-PE), was developed, and the percentage of PE+(cIgM+)_APC-(Sema3A−) cells was then calculated.

1-2-4. Light Chain Gc (Gene Conversion) Analysis According to Reversion Assay

A frozen stock of the CL18_M– cell line ($3.0\times10^6$ cells) was awaken with 10 mL of CS(–) medium, using a 25 cm$^2$ Flask, and the cells were then cultured in a $CO_2$ incubator ($39.5^\circ$ C., 5% $CO_2$). On the following day, 2 mL each of a CS(–) medium, to which each drug had been added, was added into each well of a 24 deep well plate (ThermoFisher Scientific, 95040480), and the cells were then seeded thereon to a cell density of $6.0\times10^4$ cells/mL (wherein the cell concentration and the survival rate were measured using CASY cell counter). After individual samples had been cultured for 2 days, the samples were subcultured under the same conditions to result in a cell density of $1.0\times10^4$ cells/mL. After completion of the culture for 3 days, individual samples were subcultured under the same conditions to result in a cell density of $6.0\times10^4$ cells/mL, and then, were further cultured for 2 days, so that the samples were cultured for a total of 7 days under the same conditions. At the time point of Day 7 of the culture, individual samples (in each amount of $2.0\times10^5$ cells) were transferred into each well of a 96-well plate (Nunc, 249662), and thereafter, a supernatant was removed by centrifugation at 300× g for 5 min. 200 µL each of FACS buffer was added into each well, and the cells were washed. After that, the resulting cells were centrifuged (300× g, 3 min) again, and a supernatant was then removed. This washing step was carried out repeatedly twice, and each sample was then suspended in 50 µL of FACS buffer comprising 1,000-fold diluted Goat anti-Chicken IgM Antibody FITC Conjugated. The light was shielded, and the obtained suspension was then reacted at $4^\circ$ C. for 30 min. After completion of the staining, the reaction mixture was washed with a FACS buffer twice, and each sample was then suspended in 100 µL of FACS buffer comprising 1,000-fold diluted 7-AAD, followed by measurement using FACS Canto II Flow Cytometer. Using FSC-SSC plot, dead cells, doublet cells, and 7-AAD-positive cells were removed. Thereafter, a plot, in which the vertical axis indicated FITC (Goat anti-Chicken IgM Antibody FITC Conjugated) and the longitudinal axis indicated PE (none), was developed, and the percentage of PE–_FITC+(cIgM+) cells was then calculated.

Meanwhile, after completion of the culture for 7 days, individual samples were subcultured under the same conditions to result in a cell density of $6.0\times10^4$ cells/mL. After completion of the culture for 2 days, the samples were subcultured under the same conditions to result in a cell density of $1.0\times10^4$ cells/mL. After completion of the culture for 3 days, individual samples were subcultured under the same conditions to result in a cell density of $6.0\times10^4$ cells/mL. The resulting cells were further cultured for 2 days, so that the samples were cultured for a total of 14 days under the same conditions. At the time point of Day 14 of the culture, individual samples were measured using FACS Canto II Flow Cytometer, as with the measurement on Day 7.

1-2-5. Sequence Change Analysis According to Ngs (Heavy Chain)

A frozen stock of the BMAA4-2 cell line ($3.0\times10^6$ cells) was awaken with 10 mL of CS(–) medium, using a 25 cm$^2$ Flask, and the cells were then cultured in a $CO_2$ incubator ($39.5^\circ$ C., 5% $CO_2$). On the following day, 2 mL each of a CS(–) medium, to which each drug had been added, was added into each well of a 12-well dish (Nunc, 150628), and the cells were then seeded thereon to a cell density of $6.0\times10^4$ cells/mL (wherein the cell concentration and the survival rate were measured using CASY cell counter). After individual samples had been cultured for 2 days, the samples were subcultured under the same conditions to result in a cell density of $1.0\times10^4$ cells/mL. After completion of the culture for 3 days, individual samples were subcultured in a 25 cm$^2$ Flask to result in a cell density of $6.0\times10^4$ cells/mL with respect to 10 mL of the medium under the same conditions. After completion of the culture for 2 days (Day 7 of the culture), individual samples (in each amount of $2.0\times10^6$ cells) were recovered in a 1.5-mL tube, and thereafter, a supernatant was removed by centrifugation at 1,000× g for 5 min. The residue was re-suspended in 1 mL of D-PBS(–) (Nacalai Tesque, 14249-24), and a supernatant was then removed by centrifugation at 1,000× g for 5 min. The residue was preserved at $-80^\circ$ C. Moreover, individual samples from the remaining cells were subcultured in a 12-well dish to result in a cell density of $6.0\times10^4$ cells/mL with respect to 2 mL of the medium under the same conditions. After completion of the culture for 2 days, individual samples were subcultured under the same conditions to result in a cell density of $1.0\times10^4$ cells/mL. After completion of the culture for 3 days, individual samples were subcultured in a 25 cm$^2$ Flask to result in a cell density of $6.0\times10^4$ cells/mL with respect to 10 mL of the medium under the same conditions. After completion of the culture for 2 days (Day 14 of the culture), individual samples (in each amount of $2.0\times10^6$ cells) were recovered in a 1.5-mL tube, and thereafter, a supernatant was removed by centrifugation at 1,000× g for 5 min. The residue was re-suspended in 1 mL of D-PBS(–), and a supernatant was then removed by centrifugation at 1,000× g for 5 min. The residue was preserved at $-80^\circ$ C.

(Light Chain)

A frozen stock of the BMAA4-2 cell line ($3.0\times10^6$ cells) was awaken with 10 mL of CS(–) medium, using a 25 cm$^2$ Flask, and the cells were then cultured in a $CO_2$ incubator ($39.5^\circ$ C., 5% $CO_2$). On the following day, 1 mL each of a CS(–) medium, to which each drug had been added, was added into each well of a 24-well dish, and the cells were then seeded thereon to a cell density of $3.0\times10^5$ cells/mL (wherein the cell concentration and the survival rate were measured using CASY cell counter). On the following days, individual samples were subcultured under the same conditions to result in a cell density of $1.0\times10^4$ cells/mL. After completion of the culture for 3 days, individual samples were subcultured in a 6-well dish to result in a cell density of $3.0\times10^5$ cells/mL with respect to 5 mL of the medium under the same conditions. On the following days, individual samples were subcultured in a 50-mL tube (TPP, 87050) to result in a cell density of $3.0\times10^5$ cells/mL with respect to 10 mL of the medium under the same conditions. On the following days, individual samples were subcultured again in a 50-mL tube to result in a cell density of $3.0\times10^5$ cells/mL with respect to 10 mL of the medium under the same conditions. On the following day (Day 7 of the culture), individual samples were subcultured in a 24-well dish to result in a cell density of $3.0\times10^5$ cells/mL with respect to 1 mL of the medium under the same conditions. On the following day, individual samples were subcultured under the same conditions to result in a cell density of $1.0\times10^4$ cells/mL. After completion of the culture for 3 days, individual samples were subcultured in a 50-mL tube to result in a cell density of $6.0\times10^4$ cells/mL with respect to 10 mL of the medium under the same conditions. After completion of the culture for 2 days, individual samples were subcultured under the same conditions to result in a cell density of $3.0\times10^5$ cells/mL. On the following day (Day 14 of the culture), individual samples (in each amount of 2.0×10⁶ cells) were recovered in a 1.5-mL tube, and there-after, a supernatant was then removed by centrifugation at 1,000× g for 5 min. The residue was re-suspended in 1 mL of D-PBS(-), and a supernatant was then removed by centrifugation at 1,000× g for 5 min. The residue was preserved at −80° C.

Using Wizard Genomic DNA Purification Kit (Promega, A2361), genomic DNA was extracted and purified from the cell pellets preserved at −80° C. This genomic DNA was used as a template. For the analysis of the heavy chain, using the primers BHcF1 and A001HcR-A007HcR, and also using PrimeSTAR GXL DNA Polymerase (Takara bio, R050B), after denaturation had been carried out at 98° C. for 1 min, a cycle consisting of denaturation at 98° C. for 10 sec, annealing at 58° C. for 15 sec, and an elongation reaction at 68° C. for 1 min was repeated 35 times. Finally, an elon-gation reaction at 68° C. for 5 min was carried out. Accord-ing to these protocols, PCR was carried out. On the other hand, for the analysis of the light chain, using the primers A001NGSLCF-A003NGSLCF, A005NGSLCF-A007NGSLCF, A012NGSLCF and cmNGSLcR-3B, and also using PrimeSTAR GXL DNA Polymerase, after dena-turation had been carried out at 98° C. for 1 min, a cycle consisting of denaturation at 98° C. for 10 sec, annealing at 60° C. for 15 sec, and an elongation reaction at 68° C. for 1 min was repeated 35 times. Finally, an elongation reaction at 68° C. for 5 min was carried out. According to these protocols, PCR was carried out. Using QIAquick PCR Purification Kit (Qiagen, 28106) or QIAquick Gel Extrac-tion Kit (Qiagen, 28706), each PCR product was purified, and thereafter, the concentration was measured using Nano-Drop. Individual samples (400 ng each) were mixed with one another, and thereafter, the obtained mixture was then subjected to 1% agarose gel electrophoresis, and was then purified using QIAquick Gel Extraction Kit. In these opera-tions, a washing step using PE buffer and the subsequent drying step were carried out twice, while changing the direction of the tube. The concentration of the purified DNA Mix sample was precisely measured using Quant-iT PicoGreen dsDNA Assay Kit (ThermoFisher scientific, P7589). Using GS Junior Titanium emPCR Kit (Lib-A) (Roche, Cat. No. 05 996 520 001) in accordance with the instruction manual included therewith, emulsion PCR was carried out. Then, using GS Junior Titanium Sequencing Kit (Roche, Cat. No. 05 996 554 001) and GS Junior Titanium PicoTiterPlate Kit (Roche, Cat. No. 996 619 001) in accor-dance with the instruction manuals included therewith, sequencing was carried out with GS junior (Roche Life science). After completion of the sequencing, base calling was carried out in amplicon mode, to obtain raw data (read sequences).

The read sequences outputted from the GS Junior were subjected to filtering, and when the concerned sequence did not satisfy the following three conditions, it was excluded:

(1) a read sequence comprising 250 bp or more of consecutive nucleotides of QV15 or more, (2) a read sequence, in which all frame works can be recognized by region estimation, and (3) a read sequence, in which a stop codon or a frame shift does not appear in the translation frames from CDR1 to CDR3.

With regard to the region estimation, using HMMER program (3.1b2, Johnson et al., BMC Bioinformatics. 11, 431. 2010), each region estimation profile of FW1, FW2, FW3 and FW4 according to the Kabat definition was hit, so as to determine the regions. The read sequences, in which any FW was not recognized, were excluded, and then, in the remaining read sequences, CDR1, CDR2, and CDR3 were determined based on the estimated FW regions. After completion of the filtering, 239 read sequences were ran-domly subjected to sampling without replacement, and NUS (Number of Unique Sequence) and SBL (Sum of Branch Length) were then calculated, targeting the amino acid sequences of CDR1 to CDR3. NUS indicates the number of unique amino acid sequences in the 239 sequences, whereas SBL indicates the sum of the lengths of branches of lineage trees obtained from a group of those amino acid sequences. For the production of such lineage trees, first, multiple alignment was carried out using mafft program (v7.221, Katoh & Standley, Mol. Biol. Evol. 4, 772-780. 2013), and further, a p distance matrix based on the multiple alignment results was used as input data, and a lineage tree was produced according to a neighbor-joining method, using clearcut program (1.0.9, Savolainen et al., Syst. Biol. 49, 306-362. 2000). The sampling of the 239 sequences was independently carried out 10 times, and the mean value of the NUS SBL values in each trial was determined to be the final output value.

1-2-6. Sequence Change Analysis of Anti-Hvegf-A Anti-body Generating Cell Lines According to Affinity Matura-tion and Flow Cytometry (Fcm)

Frozen stocks of the hVEGF-A #33 cell line and the hVEGF-A #44 cell line (3.0×10⁶ cells) were each awaken with a CS(-) medium, using a 25 cm² Flask (Corning, 430639), and were then cultured in a CO₂ incubator (SANYO CO₂ Incubator MCO-20AIC, 39.5° C., 5% CO₂). On the following day, the cells were seeded on a 6-well dish (Nunc, 140675) to a cell density of 1.0×10⁴ cells/mL (wherein the cell concentration and the survival rate were measured using CASY cell counter (Nepa Gene)). The cells were cultured in a CS(+) medium, in the presence or absence of a PI3Kα inhibitor (A66: 10 μM, PI3Kα Inhibitor 2: 500 nM). Moreover, after the cells had been cultured for 2 days, individual samples were subcultured under the same condi-tions to result in a cell density of 1.0×10⁴ cells/mL. Further, after completion of the culture for 3 days, individual samples were subcultured under the same conditions to result in a cell density of 6.0×10⁴ cells/mL, and the culture was continued. After completion of the culture for 2 days (Day 7 of the culture), individual samples were centrifuged to remove a supernatant, and the residue was then suspended in a CS(+) medium supplemented with 1 μM FK-506 (hereinafter referred to as a "CS/FK medium"). The suspension was centrifuged again to remove a supernatant. This washing step was carried out repeatedly twice, and individual samples were then suspended in a CS/FK medium supple-mented with AF647-labeled hVEGF-A (10 nM) and 2,000-fold diluted Goat Anti-Human IgG-PE. The light was shielded, and the obtained suspension was then reacted at 4° C. for 30 min. After completion of the staining, the reaction mixture was washed with a CS/FK medium twice, and each sample was then suspended in the CS/FK medium. There-after, using FACS Aria Fusion (BD), FCM and single cell sorting was carried out. Dead cells were removed using FSC-SSC plot. A plot, in which the vertical axis indicated AF647 (AF647-labeled hVEGF-A) and the longitudinal axis indicated PE (Goat Anti-Human IgG-PE), was developed, and the percentage of PE+(hIgG+)/AF647-(hVEGF-A-) cells was then calculated. In order to make a comparison regarding the number of cells with improved antigen-bind-ing ability according to Affinity Maturation under individual conditions, Affinity Maturation Gate was established accord-ing to the following criteria. First, the plot was converted to a contour plot in FCM analysis, and a trapezoid gate having an inclination that was in parallel with the contour of a population in which the most cells were gathered (hereinafter referred to as a "main population") was established. Next, from the contour plot of the main population, a mean value of the fluorescence intensity as an indicator of binding ability to an antigen (mean fluorescence intensity (MFI)) was calculated, and cells exhibiting MFI that was 5 or more times higher than the calculated mean value were set to enter the gate. At that time, the vertex of the trapezoid gate was set to be overlapped with the mean value MFI of the main population, and then, a cell population having low antigen-binding ability and a cell population having a low expression level of antibody were set not to enter the gate. The percentage of clones with improved antigen-binding ability was calculated by counting the number of cells existing in this Affinity Maturation Gate and then dividing the obtained value by the total number of the analyzed cells.

1-2-7. Obtainment of Antibody Variable Region Gene Sequences of Clones with Improved Antigen-Binding Ability According to Affinity Maturation, and Sequence Analysis From a cell population that corresponded to the top 0.2% of a cell population having antigen-binding ability that was improved after Affinity Maturation, 192 cells were single-cell-sorted, and were then cultured in a CS/FK medium on a 96-well plate for 8 days. From the thus cultured and growing clones, 24 clones were randomly picked up, and the gene sequence of each antibody variable region was then analyzed. According to a method of dividing heavy and light chain variable regions, which encoded the same nucleic acid sequence, into one group, the grouping of the clones was carried out. From the number of groups, the number of sequence types was calculated, and a change in the amino acid sequences was confirmed. In addition, with regard to the number of sequence changes, the original clones of each cell line were compared with clones obtained after Affinity Maturation, in terms of the nucleic acid sequence of an antibody variable region gene, and when one or more different nucleotide sequences were found, it was counted as a sequence change.

1-2-8. Measurement of Antibody Affinity of Clone with Improved Antigen-Binding Ability According to Affinity Maturation With regard to representative clones of each group, which was obtained by the grouping in the above 1-2-7, a culture supernatant was prepared, and the affinity with an antigen was then measured using an SPR method (Biacore T200, GE Healthcare). Using Human Antibody Capture Kit (BR100839, GE Healthcare), an anti-human IgG (Fc) antibody was immobilized on a CM5 sensor chip (BR100530, GE Healthcare), and an antibody contained in the culture supernatant was then captured. 25 nM hVEGF-A was reacted therewith for 240 seconds, and then, was dissociated therefrom for 500 seconds. As a regeneration solution, 3 M $MgCl_2$ was reacted with the resultant for 30 seconds, so that one cycle was completed. As a buffer, HBS–EP+(10 mM HEPES, 150 mM NaCl, 3 mM EDTA, 0.05% (v/v) surfactant P20 (pH 7.4) (BR100669, GE Healthcare)) was used, and the measurement was carried out at a flow rate of 30 μL/min. Employing Biacore T200 Evaluation Software, fitting was carried out on each SPR sensorgram according to a Langmuir 1:1 binding model, so as to calculate the association rate constant kon and the dissociation rate constant koff. Then, according to the equation: KD=koff/kon, the KD value was determined.

1-3. Results 1-3-1. Screening for Compound Promoting Diversification of Antibody Variable Region Amino Acid Sequences, Using Bmaa4-2 Cell Line Using the BMAA4-2 cell line, a system for screening for a diversification-promoting compound was constructed (FIG. 1). The BMAA4-2 cell line includes DT40 cell clones expressing anti-Sema3A antibodies (cIgM). However, if the BMAA4-2 cell line were cultured under conditions in which gene conversion (GC) or somatic hypermutation are induced, a cell population with reduced affinity for Sema3A as an antigen would appear. It is considered that the affinity of such a cell population for the antigen has been reduced as a result of changes in the amino acid sequences of variable regions. Thus, the percentage of cIgM+_Sema3A– populations under individual culture conditions is measured and compared according to FCM, so that the effect of promoting changes in the amino acid sequences (i.e., the effect of promoting the diversification of the amino acid sequences) can be evaluated.

First, from compounds that had been known to be associated with cell growth, differentiation and/or activation of B cells, gene conversion (GC), somatic hypermutation and the like, the compounds shown in Table 1 were selected. The selected compounds were each added into a medium and were then cultured. Thereafter, using, as an indicator, an increase in the cIgM+_Sema3A– populations according to FCM at the time point of 1 week after the culture, a compound promoting changes in the amino acid sequences of variable regions was screened. As a result, when Wortmannin as an inhibitor of PI3K was added, the percentage of the cIgM+_Sema3A– populations was increased in comparison to a negative control (CS(–)), and thus, Wortmannin was found to promote changes in the amino acid sequences of antibody variable regions (FIG. 2).

1-3-2. Comparison of PI3K Inhibitors in Terms of Action on Changes in Amino Acid Sequences of Antibody Variable Regions, Using Bmaa4-2 Cell Line It was found that the PI3K inhibitors have an action to promote the diversification of the amino acid sequences of antibody variable regions. Thus, next, the inhibitors shown in Table 2 were selected from among various PI3K inhibitors exhibiting different isotype specificity, and these compounds were then compared with one another, in terms of action on sequence change. The concentration of each inhibitor was determined, using $IC_{50}$ to acted molecules as a reference, according to a preliminary experiment, in which the presence or absence of isotype specificity and cytotoxicity was used as an indicator. Using the BMAA4-2 cell line, changes in the cIgM+_Sema3A– populations were compared among individual inhibitors according to FCM. As a result, it was found that the PI3Kα-specific inhibitors A66 and PI3Kα Inhibitor 2 had the highest sequence change-promoting action, and that the sequence change-promoting action of a PI3Kβ-specific inhibitor, a PI3Kδ-specific inhibitor and a PI3Kγ-specific inhibitor was lower than that of A66 or PI3Kα Inhibitor 2, or was almost at the same level as that of the negative control (CS(–)) (FIGS. 3 and 4).

Furthermore, the same experiment as described above was carried out using PI3Kα-specific inhibitors and drugs having an inhibitory activity on PI3Kα. As a result, it was confirmed that the drugs inhibiting the PI3Kα activity have an action to promote sequence changes, in comparison to the negative control (CS(–)) (FIG. 5). From these results, it became clear that drugs inhibiting PI3Kα activity promote sequence changes.

1-3-3. Verification of Action Of PI3Kα Inhibitor on Light Chain Gene Conversion (Gc) According to Reversion Assay The PI3Kα inhibitors such as A66 and PI3Kα Inhibitor 2 were found to be promising as novel diversification-promoting compounds. Hence, the action of these inhibitors was verified according to Reversion assay that had been conventionally widely used to verify GC inducing activity. The Reversion assay is a system for verifying the frequency of GC, utilizing the phenomenon that a CL18 cell line having a frame shift in the antibody light chain variable region thereof expresses IgM as a result of GC (Reversion activity) (Buerstedde et al., EMBO J. 9, 921-927. 1990). Specifically, when the percentage of cells expressing IgM is increased in the Reversion assay, it can be determined that GC is provoked in the antibody light chain variable gene region, and that the diversification of the amino acid sequence of the region is thereby promoted. Since the CL18_M– cell line used in the present assay has the property of causing toxicity due to PI3K inhibitors, PI3Kα Inhibitor 2 was used in a concentration of 200 nM in this experiment. The percentage of IgM expression-positive cells one and two weeks after the culture performed under individual conditions was calculated. As a result, it was found that A66 and PI3Kα Inhibitor 2 used as PI3Kα inhibitors exhibited higher Reversion activity than the PI3Kδ-specific inhibitor (CAL-101) and the PI3Kγ-specific inhibitors (CZC 24832 and AS 604850), and also, than a negative control (CS(–)) (FIG. 6).

1-3-4. Analysis of Antibody Variable Region Amino Acid Sequences Of PI3Kα Inhibitor-Treated Samples According to Ngs Finally, using NGS, the antibody heavy chain variable region genes of A66- and PI3Kα Inhibitor 2-treated samples were decoded, and a large-scale analysis was then performed on the amino acid sequences of the obtained antibodies. Whether the diversity of antibodies was improved in the BMAA4-2 cell population was confirmed. Using either NUC relative to the number of sequence types or SBL relative to the degree of similarity among sequences as an indicator, the A66- and PI3Kα Inhibitor 2-treated samples exhibited higher values than the negative control sample (FIG. 7).

Likewise, the antibody light chain variable region gene sequence of the A66-treated sample was also decoded, and a large-scale analysis was then performed on the amino acid sequence of the obtained antibody. As a result, in both cases of using NUS and SBL, the A66-treated sample exhibited higher values than the negative control sample (FIG. 8).

1-3-5. Screening for Compound Promoting Diversification of Antibody Variable Region Amino Acid Sequence, Using Hvegf-A–#33 Cell Line In order to select a diversification-promoting compound that was effective for DT40 cells expressing a human antibody (hIgG), using a DT40 cell line expressing an anti-hVEGF-A antibody (hIgG) (hVEGF-A–#33 cell line), and using, as an indicator, the percentage of a cell population (hIgG+_hVEGF-A–) with reduced affinity for hVEGF-A serving as an antigen, compounds were screened in the same manner as that of the above section 1-3-1 (Table 3). As a result, it was found that the percentage of hIgG+_hVEGF-A– was increased in comparison to the negative control (CS(–)) in the presence of Wortmannin, A66, PI3Kα Inhibitor 2, PF-4989216, GSK1059615, PI-103, and PIK-90. It became clear that, not only in a cell line expressing an anti-Sema3A antibody (cIgM), but also in a cell line expressing an antibody (hIgG) reacting against VEGF-A that was an antigen different from Sema3A, sequence changes were promoted by the PI3Kα inhibitors.

1-3-6. Diversification-Promoting Effects of PI3Kα Inhibitors in Affinity Maturation Using Human Antibody-Generating Cell Lines Subsequently, using A66 and PI3Kα Inhibitor 2 having the highest diversification-promoting effects in the above section 1-3-5, culture conditions for promoting Affinity Maturation were studied to both in the hVEGF-A–#33 cell line and in the hVEGF-A–#44 cell line. The hVEGF-A–#44 cell line is a DT40 cell clone expressing an anti-hVEGF-A antibody (hIgG), as with the hVEGF-A–#33 cell line. As described in the above section 1-2-6, the cells were cultured in the presence or absence of a PI3Kα inhibitor (A66: 10 μM, PI3Kα Inhibitor 2: 500 nM). After the cells had been cultured under individual culture conditions, the cultured cells were stained with AF647-labeled hVEGF-A and Goat Anti-Human IgG-PE, and were then subjected to FCM analysis. In the hIgG+_hVEGF-A+ cell population, a gate (Affinity Maturation Gate) was established, so that cells with improved binding ability to the antigen hVEGF-A (5 or more times increased in MFI) could be comprised (FIG. 9), and a comparison was then made in terms of the percentage of the cells in the gate. As a result, it was found that the percentage of the cells with improved antigen-binding ability was increased under conditions comprising A66 and PI3Kα Inhibitor 2, rather than under conditions not comprising such drugs (FIG. 10). These results suggest that the number of clones with improved antigen-binding ability was increased as a result that the PI3Kα inhibitors promoted sequence changes in the antibody variable regions of human IgG reacting against hVEGF-A. That is to say, it became clear that sequence changes in the antibody variable regions were promoted by performing Affinity Maturation under conditions comprising A66 and PI3Kα Inhibitor 2, and thus that positive clones with improved antigen-binding ability could be efficiently obtained.

1-3-7. Analysis of Antibody Variable Region Gene Sequences of Clones with Improved Antigen-Binding Ability According to Affinity Maturation, and Measurement of Antibody Affinity Furthermore, from the hVEGF-A–#33 cell line and the hVEGF-A–#44 cell line that were cultured under individual culture conditions described in the above section 1-2-6, the top 0.2% cells of a cell population with improved antigen-binding ability were isolated according to FACS. The antibody variable region gene sequences of individual growing clones were decoded, and the obtained nucleic acid sequences were then analyzed. As a result, it was found that a wide variety of sequence changes occurred in 95% or more of the obtained clones and also, changes in the amino acid sequences associated therewith occurred. Moreover, it was also confirmed that, among such clones, there were clones with improved affinity (KD value) in comparison to the original clone antibody.

From these results, it was confirmed that sequence changes in antibody variable region genes occurred in clones with improved antigen-binding ability, and accordingly, changes in the amino acid sequences and the improvement of affinity also occurred.

Industrial Applicability

The present invention relates to a method for promoting diversification of the amino acid sequences of variable regions of an antibody generated by an avian B cell population. Therefore, it is expected that the present invention will be utilized in the field of medicine and pharmacy that are associated with antibody drugs, or in the field of using antibodies as research reagents.

What is claimed is:

1. A method for promoting diversification of amino acid sequences of variable regions of an antibody generated by an avian B cell population, wherein the method comprises:

contacting a population of avian B cells with a PI3Kα inhibitor to diversify amino acid sequences of variable regions of an antibody generated by said avian B cell population; and sequencing amino acid sequences of variable regions of the antibodies generated by said avian B cell population after said contact with said PI3Kα inhibitor to confirm diversification of amino acid sequences of variable regions of said antibodies generated by said avian B cell population after contact with said PI3Kα inhibitor.

2. A method for producing an antibody comprising performing the method of claim 1 and isolating an antibody having a diversification of amino acid sequences of variable regions after said sequencing.

3. The method of claim 1, wherein the PI3Kα inhibitor is LY294002.

* * * * *

SEQUENCE LISTING

Sequence total quantity: 16
SEQ ID NO: 1                moltype = DNA   length = 41
FEATURE                     Location/Qualifiers
misc_feature                1..41
                            note = Synthetic primer
source                      1..41
                            mol_type = other DNA
                            organism = synthetic construct
SEQUENCE: 1
ctatcgcct tgccagcccg ctcagcgctc tctgcccttc c                        41

SEQ ID NO: 2                moltype = DNA   length = 54
FEATURE                     Location/Qualifiers
misc_feature                1..54
                            note = Synthetic primer
source                      1..54
                            mol_type = other DNA
                            organism = synthetic construct
SEQUENCE: 2
cgtatcgcct ccctcgcgcc atcagacgag tgcgtcgatg acttcggtcc cgtg          54

SEQ ID NO: 3                moltype = DNA   length = 54
FEATURE                     Location/Qualifiers
misc_feature                1..54
                            note = Synthetic primer
source                      1..54
                            mol_type = other DNA
                            organism = synthetic construct
SEQUENCE: 3
cgtatcgcct ccctcgcgcc atcagacgct cgacacgatg acttcggtcc cgtg          54

SEQ ID NO: 4                moltype = DNA   length = 53
FEATURE                     Location/Qualifiers
misc_feature                1..53
                            note = Synthetic primer
source                      1..53
                            mol_type = other DNA
                            organism = synthetic construct
SEQUENCE: 4
cgtatcgcct ccctcgcgcc atcagagacg cactcgatga cttcggtccc gtg           53

SEQ ID NO: 5                moltype = DNA   length = 54
FEATURE                     Location/Qualifiers
misc_feature                1..54
                            note = Synthetic primer
source                      1..54
                            mol_type = other DNA
                            organism = synthetic construct
SEQUENCE: 5
cgtatcgcct ccctcgcgcc atcagagcac tgtagcgatg acttcggtcc cgtg          54

SEQ ID NO: 6                moltype = DNA   length = 54
FEATURE                     Location/Qualifiers
misc_feature                1..54
                            note = Synthetic primer
source                      1..54
                            mol_type = other DNA
                            organism = synthetic construct
SEQUENCE: 6
cgtatcgcct ccctcgcgcc atcagatcag acacgcgatg acttcggtcc cgtg          54

SEQ ID NO: 7                moltype = DNA   length = 54
FEATURE                     Location/Qualifiers
misc_feature                1..54
                            note = Synthetic primer
source                      1..54
                            mol_type = other DNA
                            organism = synthetic construct
SEQUENCE: 7
cgtatcgcct ccctcgcgcc atcagatatc gcgagcgatg acttcggtcc cgtg          54

SEQ ID NO: 8                moltype = DNA   length = 54
FEATURE                     Location/Qualifiers
misc_feature                1..54
                            note = Synthetic primer
source                      1..54
                            mol_type = other DNA
                            organism = synthetic construct -continued

```
SEQUENCE: 8
cgtatcgcct ccctcgcgcc atcagcgtgt ctctacgatg acttcggtcc cgtg          54

SEQ ID NO: 9              moltype = DNA   length = 54
FEATURE                   Location/Qualifiers
misc_feature              1..54
                          note = Synthetic primer
source                    1..54
                          mol_type = other DNA
                          organism = synthetic construct
SEQUENCE: 9
cgtatcgcct ccctcgcgcc atcagacgag tgcgtcaggt tccctggtgc aggc          54

SEQ ID NO: 10             moltype = DNA   length = 54
FEATURE                   Location/Qualifiers
misc_feature              1..54
                          note = Synthetic primer
source                    1..54
                          mol_type = other DNA
                          organism = synthetic construct
SEQUENCE: 10
cgtatcgcct ccctcgcgcc atcagacgct cgacacaggt tccctggtgc aggc          54

SEQ ID NO: 11             moltype = DNA   length = 53
FEATURE                   Location/Qualifiers
misc_feature              1..53
                          note = Synthetic primer
source                    1..53
                          mol_type = other DNA
                          organism = synthetic construct
SEQUENCE: 11
cgtatcgcct ccctcgcgcc atcagagacg cactcaggtt ccctggtgca ggc           53

SEQ ID NO: 12             moltype = DNA   length = 54
FEATURE                   Location/Qualifiers
misc_feature              1..54
                          note = Synthetic primer
source                    1..54
                          mol_type = other DNA
                          organism = synthetic construct
SEQUENCE: 12
cgtatcgcct ccctcgcgcc atcagatcag acacgcaggt tccctggtgc aggc          54

SEQ ID NO: 13             moltype = DNA   length = 54
FEATURE                   Location/Qualifiers
misc_feature              1..54
                          note = Synthetic primer
source                    1..54
                          mol_type = other DNA
                          organism = synthetic construct
SEQUENCE: 13
cgtatcgcct ccctcgcgcc atcagatatc gcgagcaggt tccctggtgc aggc          54

SEQ ID NO: 14             moltype = DNA   length = 54
FEATURE                   Location/Qualifiers
misc_feature              1..54
                          note = Synthetic primer
source                    1..54
                          mol_type = other DNA
                          organism = synthetic construct
SEQUENCE: 14
cgtatcgcct ccctcgcgcc atcagcgtgt ctctacaggt tccctggtgc aggc          54

SEQ ID NO: 15             moltype = DNA   length = 53
FEATURE                   Location/Qualifiers
misc_feature              1..53
                          note = Synthetic primer
source                    1..53
                          mol_type = other DNA
                          organism = synthetic construct
SEQUENCE: 15
cgtatcgcct ccctcgcgcc atcagcgaga gatacaggtt ccctggtgca ggc           53

SEQ ID NO: 16             moltype = DNA   length = 45
FEATURE                   Location/Qualifiers
misc_feature              1..45
                          note = Synthetic primer
source                    1..45
                          mol_type = other DNA
```

-continued

```
                    organism = synthetic construct
SEQUENCE: 16
ctatgcgcct tgccagcccg ctcagatgtc acaatttcac gatgg                    45
```